United States Patent [19]
Rivier et al.

[11] Patent Number: 5,098,995
[45] Date of Patent: Mar. 24, 1992

[54] GRF ANALOGS VIIA

[75] Inventors: Jean E. F. Rivier; Wylie W. Vale, Jr.; Catherine L. Rivier, all of La Jolla, Calif.

[73] Assignee: The Salk Institute For Biological Studies, San Diego, Calif.

[21] Appl. No.: 342,751

[22] Filed: Apr. 25, 1989

Related U.S. Application Data

[63] Continuation-in-part of Ser. No. 53,235, May 22, 1987, Pat. No. 5,002,931.

[51] Int. Cl.$^5$ .......................... C07K 7/10; A61K 37/02
[52] U.S. Cl. .................................................... 530/324
[58] Field of Search ........................... 530/324; 514/12

[56]     References Cited
U.S. PATENT DOCUMENTS 4,594,329  6/1986  Vale, Jr. et al. ........................ 514/12
4,728,726  3/1988  Rivier et al. ........................... 530/324

OTHER PUBLICATIONS

Gubler et al., Pro. Natl. Acad. Sci., vol. 80, 1983, pp. 4311–4314

Ling et al., Pro. Natl. Acad. Sci., vol. 81, 1984, pp. 4302–4306

Primary Examiner—Lester L. Lee
Assistant Examiner—A. Davenport
Attorney, Agent, or Firm—Fitch, Even, Tabin & Flannery

[57]          ABSTRACT

The invention provides synthetic peptides which are extremely potent in stimulating the release of pituitary GH in animals, including humans and also resist enzymatic degradation in the body. The peptides have the sequence: (B)$R_1$-$R_2$-$R_3$-Ala-($Q_1$)$R_5$-Phe-Thr-$R_8$-Ser($Q_2$)$R_{10}$-Arg-$R_{12}$-($Q_3$)$R_{13}$-Leu-$R_{15}$-Gln-($Q_4$)Leu-$R_{18}$-($Q_5$)Ala-Arg-$R_{21}$-($Q_6$)$R_{22}$-($Q_7$)Leu-$R_{24}$-$R_{25}$-($Q_8$)$R_{26}$-($Q_9$)$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr, D-Tyr, Met, Phe, D-Phe, pCl-Phe, Leu, His or D-His; B is H, $C^\alpha$Me, $N^\alpha$Me, desamino, Ac or For; $R_2$ is Ala, D-Ala, NMA or D-NMA; $R_3$ is Asp or D-Asp; $R_5$ is Ile or Leu; $R_8$ is Ser, Asn, Lys, Arg, Asp or Glu; $R_{10}$ is Tyr, D-Tyr or Phe; $R_{12}$ is Arg or Lys; $R_{13}$ is Ile, Val, Leu or Ala; $R_{15}$ is Gly or Ala; $R_{18}$ is Ser or Tyr; $R_{21}$ is Lys, D-Lys, Arg or D-Arg; $R_{22}$ is Leu, Ile, Ala or Val; $R_{24}$ is Gln or His; $R_{25}$ is Asp or Glu; $R_{26}$ is Ile or Leu; $R_{27}$ is Met, D-Met, Ala, Nle, Ile, Leu, Nva or Val; $R_{28}$ is Asn or Ser; $R_{34}$ is Ser or Arg; $R_{38}$ is Arg or Gln; $R_{39}$ is Gly or Arg; $R_{40}$ is Ala or Ser; $R_{42}$ is Phe, Ala or Val; $R_{43}$ is Asn or Arg; $R_{44}$ is a natural amino acid; $Q_1$–$Q_9$ are either H or $C^\alpha$Me, provided however that one of $Q_1$–$Q_9$ is $C^\alpha$Me. These peptides may also be used diagnostically, and the C-terminus can be shortened to residue-29.

2 Claims, No Drawings

GRF ANALOGS VIIA

This invention was made with Government support under Grant No. PO1-DK-26741, awarded by the Department of Health and Human Services (NIH). The Government has certain rights in this invention.

This application is a continuation-in-part of our pending application Ser. No. 053,235, filed May 22, 1987, issued Mar. 26, 1991, U.S. Pat. No. 5,002,931.

The present invention relates to peptides having influence on the function of the pituitary gland in humans and other animals. In particular, the present invention is directed to peptides which promote the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. A hypothalamic inhibitory factor was characterized in 1972 in the form of somatostatin which inhibits the secretion of growth hormone(GH). In 1982, human pancreatic (tumor) releasing factors (hpGRF) were isolated from extracts of human pancreatic tumors, purified, characterized, synthesized and tested, which were found to promote the release of GH by the pituitary. Both of these hypophysiotropic factors have been reproduced by total synthesis, and analogs of the native structures have been synthesized. Human hypothalamic GH releasing factor has precisely the same structure; thus, the term hGRF is used hereinafter.

SUMMARY OF THE INVENTION

Synthetic polypeptides have now been synthesized and tested which release GH from cultured pituitary cells, which have increased resistence to enzymatic degradation in the body, and which exhibit very substantially increased potency. It is believed that these advantageous properties result from the peptides having an alpha-helical form of increased stability. These peptides have at least one residue in one or more of positions 5, 10, 13, 17, 19, 22, 26 and 27 that is substituted with a methyl group on its alpha carbon atom ($C^\alpha Me$), and preferably several of these residues are so substituted. Ala having its alpha carbon atom substituted with a methyl group is indicated by the abbreviation CMA or Aib (for amino-isobutyric acid), whereas Leu having its alpha carbon atom substituted with a methyl group is indicated by CML.

In addition to the foregoing, the peptides may contain other substitutions for various residues fround in the native hormones. For example, D-Ala, $N^\alpha CH3$-D-Ala(D-NMA) or NMA may be substituted in the 2-position. Either $C^\alpha MeLeu$(CML) or Nle is preferably present instead of Met in the 27-position; however, D-Met or Nva or other residues may be present. The peptides may also have one of the following residues in the 1-position: Tyr, D-Tyr, Met, Phe, D-Phe, pCl-Phe, Leu, His and D-His, which residue may optionally have a methyl substitution either on the alpha-carbon or in the alpha-amino group, or the alpha-amino group may be deleted (desamino); this residue may also have its alpha-amino group acylated, preferably by acetyl (Ac) or formyl (For). The peptides may optionally contain other substitutions as are known in the art, e.g., D-Asp at the 3-position and/or Arg at the 12-position and/or Phe or D-Tyr at the 10-position and/or Ala at the 15-position and/or Asn in the 28-position.

Pharmaceutical compositions in accordance with the invention include such analogs which are between about 29 and 44 residues in length, or a nontoxic salt of any of these, dispersed in a pharmaceutically or veterinarily acceptable liquid or solid carrier. Such pharmaceutical compositions can be used in clinical medicine, both human and veterinary, for administration for therapeutic purposes, and also diagnostically. Moreover, they can be used to promote the growth of warm-blooded animals, including fowl, and in aquiculture

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated. D-NMA signifies the D-isomer of alanine wherein the alpha-amino group is subtituted by methyl.

The invention generally provides synthetic peptides having the following sequence (I): (B)R1-R2-R3-Ala-($Q_1$)$R_5$-Phe-Thr-$R_8$-Ser-($Q_2$)$R_{10}$-Arg-$R_{12}$-($Q_3$)$R_{13}$-Leu-$R_{15}$-Gln-($Q_4$)Leu-$R_{18}$-($Q_5$)Ala-Arg-$R_{21}$-($Q_6$)$R_{22}$-($Q_7$)Leu-$R_{24}$-$R_{25}$-($Q_8$)$R_{26}$-($Q_9$)$R_{27}$-$R_{28}$-Arg-Gln-Gln-Gly-Glu-$R_{34}$-Asn-Gln-Glu-$R_{38}$-$R_{39}$-$R_{40}$-Arg-$R_{42}$-$R_{43}$-$R_{44}$ wherein $R_1$ is Tyr, D-Tyr, Met,Phe, D-Phe, pCl-Phe, Leu, His or D-His; B is H, $C^\alpha Me$, $N^\alpha Me$, desamino, Ac or For; $R_2$ is Ala, D-Ala, NMA or D-NMA; $R_3$ is Asp or D-Asp; $R_5$ is Ile or Leu; $R_8$ is Ser, Asn, Lys, Arg, Asp or Glu; $R_{10}$ is Tyr, D-Tyr or Phe; $R_{12}$ is Arg or Lys; $R_{13}$ is Ile, Val, Leu or Ala; $R_{15}$ is Gly or Ala; $R_{18}$ is Ser or Tyr; $R_{21}$ is Lys, D-Lys, Arg or D-Arg; $R_{22}$ is Leu, Ile, Ala or Val; $R_{24}$ is Gln or His; $R_{25}$ is Asp or Glu; $R_{26}$ is Ile or Leu; $R_{27}$ is Met, D-Met, Ala, Nle, Ile, Leu, Nva or Val; $R_{28}$ is Asn or Ser; $R_{34}$ is Ser or Arg; $R_{38}$ is Arg or Gln; $R_{39}$ is Gly or Arg; $R_{40}$ is Ala or Ser; $R_{42}$ is Phe, Ala or Val; $R_{43}$ is Asn or Arg; $R_{44}$ is a natural amino acid; $Q_1$-$Q_9$ are either H or $C^\alpha Me$, provided however that all of the residues between $R_{30}$ and $R_{44}$, inclusive, or any portion thereof may be deleted, beginning at the C-terminus, and provided further that at least one of $Q_1$-$Q_9$ is $C^\alpha Me$. In one preferred subclass of the foregoing, $R_5$ is Ile, $R_{18}$ is Ser, $R_{24}$ is Gln, $R_{25}$ is Asp, $R_{26}$ is Ile, $R_{34}$ is Ser, $R_{38}$ is Arg, $R_{39}$ is Gly and $R_{40}$ is Ala. If the peptide extends to position-44, $R_{44}$ is preferably Leu or Val.

Another preferred subclass is the peptides having the following sequence: (B) $R_1$-$R_2$-$R_3$-Ala-($Q_1$)Ile-Phe-Thr-$R_8$-Ser-($Q_2$)$R_{10}$-Arg-$R_{12}$-($Q_3$)$R_{13}$-Leu-$R_{15}$-Gln-($Q_4$)Leu-Ser-($Q_5$)Ala-Arg-$R_{21}$-($Q_6$)$R_{22}$-($Q_7$)Leu-Gln-Asp-($Q_8$)Ile-($Q_9$)$R_{27}$-$R_{28}$-Arg-Gln-Gln-Gly-Glu-Ser-Asn-Gln-Glu-Arg-Gly-Ala-Arg-$R_{42}$-$R_{43}$-$R_{44}$ wherein $R_1$ is Tyr, D-Tyr, Met, Phe, D-Phe, pCl-Phe, Leu, His or D-His; B is H, $C^\alpha Me$, $N^\alpha Me$, desamino, Ac or For; $R_2$ is Ala, D-Ala, NMA or D-NMA; $R_3$ is Asp or D-Asp; $R_8$ is Ser, Asn, Lys, Arg, Asp or Gln; $R_{10}$ is Tyr, D-Tyr or Phe; $R_{12}$ is Arg or Lys; $R_{13}$ is Ile, Val, Leu or Ala; $R_{15}$ is Gly or Ala; $R_{21}$ is Lys, D-Lys, Arg or D-Arg; $R_{22}$ is Leu, Ile, Ala or Val; $R_{27}$ is Met, D-Met, Ala, Nle, Ile, Leu, Nva or Val; $R_{28}$ is Asn or Ser; $R_{42}$ is Phe, Ala or Val; $R_{43}$ is Asn or Arg; $R_{44}$ is a natural amino acid; $Q_1$-$Q_9$ are either H or $C^aMe$, provided however that any or all of the residues between $R_{30}$ and $R_{44}$, inclusive, may be deleted in sequence beginning at the C-terminus and provided that at least one of $Q_1$-$Q_9$ is $C^aMe$. In any of these peptides, the carboxyl moiety of the amino acid residue at the C-terminus may be any of the following radicals: —COOR, —CRO, —CONHNHR, —CON(R)(R') or —CH$_2$OR, with R and R' being lower alkyl, fluoro lower alkyl or hydrogen; methyl, ethyl and propyl are the preferred lower alkyl groups. Preferably it is —CONHR, with R being H or lower alkyl.

Still another preferred subclass of peptides provided by the invention are those according to the formula:

(B)$R_1$-$R_2$-Asp-Ala-($Q_1$)Ile-Phe-Thr-R$_8$-Ser-($Q_2$)$R_{10}$-Arg-$R_{12}$-($Q_3$)$R_{13}$-Leu-$R_{15}$-Gln-($Q_4$)Leu-$R_{18}$-($Q_5$)Ala-Arg-$R_{21}$-($Q_6$)$R_{22}$-($Q_7$)Leu-$R_{24}$-$R_{25}$-($Q_8$)$R_{26}$-($Q_9$)$R_{27-28}$-Arg-Gln-Gln-Gly-Y wherein $R_1$ is Tyr, D-Tyr, Phe, D-Phe, His or D-His; B is H, $C^aMe$ or $N^aMe$; $R_2$ is Ala, D-Ala, NMA or D-NMA; $R_8$ is Ser, Asn, Lys, Arg, Asp or Glu; $R_{10}$ is Tyr, D-Tyr or Phe; $R_{12}$ is Arg or Lys; $R_{13}$ is Ile, Val, Leu or Ala; $R_{15}$ is Gly or Ala; R18 is Ser or Tyr; $R_{21}$ is Lys, D-Lys, Arg or D-Arg; $R_{22}$ is Leu, Ile, Ala or Val; $R_{24}$ is Gln or His; $R_{25}$ is Asp or Glu; $R_{26}$ is Ile or Leu $R_{27}$ is Met, Ala, Nle, Ile, Leu, Nva or Val; $R_{28}$ is Asn or Ser; Y is NHR with R being H or lower alkyl; $Q_1$-$Q_9$ are either H or $C^aMe$, provided however that Gly, Gln-Gly or Gln-Gln-Gly may be deleted at the C-terminus, and provided also that at least one of $Q_1$-$Q_9$ is $C^aMe$.

As defined above, fragments which extend from the N-terminus through residue-29 have biological potency in effecting the release of GH by the pituitary, and such biologically active fragments of 29 or 32 residues in length which have a C-terminus that is an amide or a substituted amide are most preferred. When the peptide has 40 or more residues, there is no clear preference for the moiety at the C-terminus.

The peptides are synthesized by a suitable method, such as by exclusively solid-phase techniques, by partial solid-phase techniques, by fragment condensation or by solution couplings. For example, techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

In this respect, the present invention creates intermediates of the Formula (II): $X^1$-(B)$R_1$(X or $X^2$)-$R_2$-$R_3$($X^3$)-Ala-($Q_1$)$R_5$-Phe-Thr($X^4$)-$R_8$($X^8$)-Ser($X^4$)-($Q_2$)$R_{10}$($X^2$)-Arg($X^6$)-$R_{12}$($X^6$ or $X^7$)-($Q_3$)$R_{13}$-Leu-$R_{15}$-Gln($X^5$)-($Q_4$)Leu-$R_{18}$($X^2$ or $X^4$)-($Q_5$)Ala-Arg($X^6$)-$R_{21}$($X^6$ or $X^7$)-($Q_6$)$R^{22}$-($Q^7$)Leu-$R^{24}$($X^5$ or X)-$R_{25}$($X^3$)-($Q_8$)$R_{26}$-($Q_9$)$R_{27}$-$R_{28}$($X^4$ or $X^5$)-Arg($X^6$)-Gln($X^5$)-Gln($X^5$)-Gly-Glu($X^3$)-$R_{34}$($X^4$ or $X^6$)-Asn($X^5$)-Gln($X^5$)-Glu($X^3$)-$R_{38}$($X^6$ or $X^5$)-$R_{39}$($X^6$)-$R_{40}$($X^2$)-Arg($X^6$)-$R_{42}$-$R_{43}$($X^5$ or $X^6$)-$R_{44}$($X^8$)-$X^9$ wherein:

$X^1$ is either hydrogen or an alpha-amino protecting group. The alpha-amino protecting groups contemplated by $X_1$ are those well known to be useful in the art of stepwise synthesis of polypeptides. Among the classes of alpha-amino protecting groups which may be employed as $X^1$ are (1) aromatic urethan-type protecting groups, such as fluorenylmethyloxycarbonyl (FMOC), benzyloxycarbonyl(Z) and substituted Z, such as p-chlorobenzycoxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred alpha-amino protecting group is BOC, even when an $N^a$Me-substituted residue is employed in the 1-position; of course $X^1$ is H when B is desamino.

X is hydrogen or a protecting group for the imidazole nitrogen of His, such as Tos.

$X^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl. $X^2$ can be hydrogen which means that there is no side-chain protecting group on the amino acid residue in that position.

$X^3$ is hydrogen or a suitable ester-forming protecting group for the carboxyl group of Asp or Glu, such as benzyl(OBzl), 2,6-dichlorobenzyl, methyl and ethyl.

$X^4$ may be a suitable protecting group for the hydroxyl group of Thr or Ser, such as acetyl, benzoyl, tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a suitable protecting group for the side chain amido group of Asn or Gln. It is preferably xanthyl(Xan).

$X^6$ is a suitable protecting group for the guanido group of Arg, such as nitro, Tos, CBZ, adamantyloxycarbonyl, and BOC, or is hydrogen.

$X^7$ is hydrogen or a suitable protecting group for the side chain amino group of Lys. Illustrative of suitable side chain amino protecting groups are 2-chlorobenzyloxycarbonyl(2-Cl-Z), Tos, t-amyloxycarbonyl and BOC.

$X^8$ is hydrogen or a suitable side-chain protecting group as generally specified above.

Met can optionally be protected by oxygen, but is preferably left unprotected.

The selection of a side chain amino protecting group is not critical except that generally one is chosen which is not removed during deprotection of the alpha-amino groups during the synthesis. However, for some amino acids, e.g. His, protection is not generally necessary after coupling is completed, and the protecting groups may be the same.

$X^9$ is a suitable protecting group for the C-terminal carboxyl group, such as the ester-forming group $X^{3,}$ or is an anchoring bond used in solid-phase synthesis for linking to a solid resin support, or is des-$X^{9,}$ in which case the residue at the C-terminus has a carboxyl moiety which is Y, as defined herein-before. When a solid resin support is used, it may be any of those known in the art, such as one having the formulae: —O—CH2-resin support, —NH-benzhydrylamine (BHA) resin support or —NH-paramethylbenzhydrylamine (MBHA) resin support. When the unsubstituted amide is desired, use of BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it may be preferable to sythesize the peptide using solution synthesis methods as set forth in the Houben-Weyl text.

In the formula for the intermediate, at least one of the X-groups is a protecting group or $X^9$ includes resin support. Thus, the invention also provides a method for manufacturing a peptide of interest by (a) forming a peptide having at least one protective group and the formula (II): wherein: X, $X^1$, $X^2$, $X^3$, $X^4$, $X^5$, $X^6$, $X^7$ and $X^8$ are each either hydrogen or a protective group and $X^9$ is either a protective group or an anchoring bond to resin support or is des-$X^9$, in which case the residue at the C-terminus may have the desired carboxy moiety; (b) splitting off the protective group or groups or anchoring bond from the peptide of the formula (II); and (c) if desired, converting the resulting peptide of the sequence (I) into a nontoxic salt thereof.

In selecting a particular side chain protecting group to be used in the synthesis of the peptides, the following general rules are followed: (a) the protecting group preferably retains its protecting properties and is not be split off under coupling conditions, (b) the protecting group should be stable to the reagent and, with the exception of Xan, is preferably stable under the reaction conditions selected for removing the alpha-amino protecting group at each step of the synthesis, and (c) the side chain protecting group must be removable, upon the completion of the synthesis containing the desired amino acid sequence, under reaction conditions that will not undesirably alter the peptide chain.

The peptides are preferably prepared using solid phase synthesis, such as that generally described by Merrifield, *J. Am. Chem. Soc.,* 85, p 2149 (1963), although other equivalent chemical syntheses known in the art can also be used as previously mentioned. Solid-phase synthesis is commenced from the C-terminus of the peptide by coupling a protected alpha-amino acid to a suitable resin. Such a starting material can be prepared by attaching an alpha-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6. BHA and MBHA resin supports are commercially available and are generally used only when the desired polypeptide being synthesized has an unsubstituted amide at the C-terminal.

The C-terminal amino acid, e.g. Asn, protected by BOC and by Xan, can be first coupled to the chloromethylated resin according to the procedure set doerh in *Chemistry Letters,* K. Horiki et al. 165-168 (1978), using KF in DMF at about 60° C. for 24 hours with stirring, when for example a 43-residue free acid analog of rat GRF(rGRF) is to be synthesized. Following the coupling of the BOC-protected amino acid to the resin support, the alpha-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific alpha-amino protecting groups may be used as described in Schroder & Lubke, "The Peptides", 1 pp 72-75 (Academic Press 1965).

After removal of the alpha-amino protecting group, the remaining alpha-amino- and side-chain-protected amino acids are coupled stepwise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly uitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.,* 59, pp 1-27 (1970).

Each protected amino acid or amino acid sequence is introduced into the solid phase reactor in about a fourfold or more excess, and the coupling may be carried out in a medium of dimethylformamide(DMF):$CH_2Cl_2$ (1:1) or in DMF or $CH_2Cl_2$ alone. In cases where incomplete coupling occurs, the coupling procedure is repeated before removal of the alpha-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers.* 1978, 17, pp 1927-1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups X, $X_2$, $X_3$, $X_4$, $X^5$, $X^6$, $X^7$ and $X^8$ and the anchoring bond $X^9$ and also the alpha-amino protecting group $X^1$ if one is used, to obtain the peptide in the form of the free acid. If Met is present in the sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, anisole and methylethyl sulfide are included as scavengers in the reaction vessel.

The following Example 1 sets forth a preferred method for synthesizing peptides by the solid-phase technique. It will of course be appreciated that the synthesis of a correspondingly longer peptide is effected in the same manner by merely adding the requisite number of amino acids at the C-terminus of the chain. It is presently felt that biologically active fragments should contain the indicated sequence at the N-terminus, and addition of residues to the N-terminus is not considered advantageous.

EXAMPLE 1

The synthesis of the peptide [$N^\alpha$MeTyr$^1$, Ala$^{15}$, CML$^{27}$, Asn$^{28}$]-hGRF(1-29)-NH$_2$ having the formula: $N^\alpha$MeTyr-Ala-Asp-Ala-Ile-Phe-Thr-Asn-Ser-Tyr-Arg-Lys-Val-Leu-Ala-Gln-Leu-Ser-Ala-Arg-Lys-Leu-Leu-Gln-Asp-Ile-CML-Asn-Arg-NH$_2$ is conducted in a stepwise manner using a Beckman 990 peptide synthesizer on a commercially available MBHA resin as generally described in Vale et al. U.S. Pat. No. 4,292,313. Coupling of BOC-Arg(Tos) to the resin results in the substitution of about 0.35 mmol. Arg per gram of resin.

After deblocking and neutralization, the peptide chain is built step-by-step on the resin. Deblocking, neutralization and addition of each amino acid is performed in general accordance with the procedure set forth in detail in Rivier, J., *J. Amer. Chem. Soc.*, 96, 2986-2992 (1974). All solvents that are used are carefully degassed by sparging with an inert gas, e.g. helium or nitrogen, to insure the absence of oxygen that might undesirably oxidize the sulfur of the Met residue.

Deblocking is preferably carried out in accordance with Schedule A which follows:

| SCHEDULE A | |
|---|---|
| Reagent | Mixing time (Min.) |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |
| 7. MeOH (twice) | 0.5 |
| 8. CH$_2$Cl$_2$ (twice) | 0.5 |

The couplings are preferably carried out as set out in Schedule B which follows:

| SCHEDULE B | |
|---|---|
| Reagent | Mixing time (Min.) |
| 9. DCCI | — |
| 10. Boc-amino acid | 50-90 |
| 11. MeOH (twice) | 0.5 |
| 12. CH$_2$Cl$_2$ (twice) | 0.5 |
| 13. Ac$_2$O (3M) in CH$_2$Cl$_2$ | 15.0 |
| 14. CH$_2$Cl$_2$ | 0.5 |

| -continued | |
|---|---|
| SCHEDULE B | |
| Reagent | Mixing time (Min.) |
| 15. MeOH | 0.5 |
| 16. CH$_2$Cl$_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(Tos) is being coupled, a mixture of 50% DMF and methylene chloride is used. Bzl ether is used as the hydroxyl side-chain protecting roup for Ser and Thr. The amido group of Asn or Gln is protected by Xan when DCC coupling is used as is preferred. P-nitrophenyl ester(ONp) may also be used to activate the carboxyl end of Asn or Gln, and for example, BOC-Asn(ONp) can be coupled overnight using one equivalent of HOBt in a 50% mixture of DMF and methylene chloride, in which case no DCC is added. 2-chloro-benzyloxycarbonyl(2Cl-Z) is used as the protecting group for the Lys side chain. Tos is used to protect the guanido group of Arg and the imidazole nitrogen of His, and the Glu or Asp side-chain carboxyl group is protected with OBzl. The phenolic hydroxyl group of Tyr is protected with 2,6-dichlorobenzyl(DCB). At the end of the synthesis, the following composition is obtained: BOC-$N^\alpha$MeTyr($X^2$)-Ala-Asp-($X^3$)-Ala-Ile-Phe-Thr($X^4$)-Asn($X^5$)-Ser($X^4$)-Tyr($X^2$)-Arg($X^6$)-Lys($X^7$)-Val-Leu-Ala-Gln($X^5$)-Leu-Ser($X^4$)-Ala-Arg($X^6$)-Lys($X^7$)-Leu-Leu-Gln($X^5$)-Asp($X^3$)-Ile-CML-Asn($X^5$)-Arg($X^6$)-X9 wherein $X^2$ is DCB, $X^3$ is OBzl, $X^4$ is Bzl, $X^5$ is Xan, $X^6$ is Tos, $X^7$ is 2Cl-Z and $X^9$ is NH-MBHA-resin support. Xan may have been partially or totally removed by TFA treatment used to deblock the alpha-amino protecting group.

In order to cleave and deprotect the protected peptide-resin, it is treated with 1.5 ml. anisole, 0.5 ml. methylethylsulfide and 15 ml. hydrogen fluoride(HF) per gram of peptide-resin, at $-20°$ C. for one-half hour and at $0°$ C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The cleaved and deprotected peptide is then dissolved in 0-5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp 125-8 and Marki et al. *J. Am. Chem. Soc.* 103, 3178 (1981). Cartridges fitting Waters Associates prep LC-500 are packed with 15-20$\mu$C$_{18}$ Silica from Vydac (300A). A gradient of CH$_3$CN in TEAP is generated by a low pressure Eldex gradient maker, as in Rivier, J., *J. Liq. Chromatoqraphy* 1, 343-367 (1978). The chromatographic fractions are carefully monitored by HPLC, and only the fractions showing substantial purity are pooled. Desalting of the purified fractions, independently checked for purity, is achieved using a gradient of CH$_3$CN in 0.1% TFA. The center cut is then lyophilized to yield the desired peptide, the purity of which should be greater than 98%.

The optical rotation of the purified peptide is measured using a Perkin-Elmer polorimeter and found to be $[\alpha]_D = -52.0 \pm 1$ (c=1, 1% acetic acid).

EXAMPLE 2

The synthesis of a 40-residue amidated peptide [C$^a$MeHis$^1$, D-NMA$^2$, CML$^{27}$]-hGRF(1-40)-NH$_2$ having the formula: H-C$^a$MeHis-D-NMA-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-CML-Ser-Arg-Gly-Ala-NH$_2$ is conducted in a stepwise manner using a Beckman 990 Peptide Synthesizer on an MBHA resin as generally described in Vale et al. U.S. Pat No. 4,292,313. The peptide is judged to be substantially pure using TLC and HPLC.

EXAMPLE 3

The synthesis of [D-NMA$^2$, CML$^{27}$]-rGRF(1-43)-OH having the formula: H-His-D-NMA-Asp-Ala-Ile-Phe-Thr-Ser-Ser -Tyr-Arg-Arg-Ile-Leu-Gly-Gln-Leu-Tyr-Ala-Arg-Lys-Leu-Leu -His-Glu-Ile-CML-Asn-Arg-Gln-Gln-Gly-Glu-Arg-Asn-Gln-Glu -Gln-Arg-Ser-Arg-Phe-Asn-OH is conducted in a stepwise manner using a Beckman 990 Peptide Synthesizer, using a chloromethylated resin with initial coupling as described in *Chemistry Letters, supra.* and thereafter in the manner generally described in Example 1. The peptide is judged to be substantially pure using TLC and HPLC.

EXAMPLE 4

The synthesis of the hGRF analog fragment, [N$^a$Me-Tyr$^1$, Lys$^8$, Ala$^{15}$, CML$^{27}$, Asn$^{28}$]-hGRF(1-29)-NH$_2$ having the formula: N$^a$MeTyr-Ala-Asp-Ala-Ile-Phe-Thr-Lys-Ser-Tyr-Arg-Lys-Val-Leu-Ala-Gln-Leu-Ser-Ala-Arg -Lys-Leu-Leu-Gln-Asp-Ile-CML-Asn-Arg-NH$_2$ is conducted in a stepwise manner using a Beckman 990 Peptide Synthesizer on an MBHA resin as in Example 1. This analog is judged to be substantially pure using TLC and HPLC.

The synthesis is repeated changing the N-terminal residue to produce [N$^a$MeHis$^1$, Lys$^8$, Ala$^{15}$, CML$^{27}$, Asn$^{28}$]-hGRF(1-29)-NH$_2$

EXAMPLE 5

The synthesis of the hGRF analog fragment [N$^a$Me-Tyr$^1$, D-Lys$^{21}$, CML$^{27}$]-hGRF(1-29)-NH$_2$ having the formula: N$^a$MeTyr-Ala-Asp-Ala-Ile-Phe-Thr-Asn-Ser-Tyr-Arg -Lys-Val-Leu-Gly-Gln-Leu-Ser-Ala-Arg-D-Lys-Leu-Leu-Gln -Asp-Ile-CML-Ser-Arg-NH2 is conducted in a stepwise manner using a Beckman 990 Peptide Synthesizer on an MBHA resin as in Example 1. The peptide is judged to be substantially pure using TLC and HPLC.

EXAMPLE 6

The synthesis of [N$^a$MeHisl, D-NMA$^2$, D-Arg$^{21}$, CML$^{27}$]-rGRF(1-29)-NH$_2$, having the formula: N$^a$Me-His-D-NMA-Asp-Ala-Ile-Phe-Thr-Lys-Ser-Tyr-Arg-Arg-Ile -Leu-Gly-Gln-Leu-Try-Ala-Arg-D-Arg-Leu-Leu-His-Glu-Ile -CML-Asn-Arg-NH2 is conducted in a stepwise manner using a Beckman 990 Peptide Synthesizer on an MBHA resin as in Example 1. The peptide is judged to be substantially pure using TLC and HPLC.

EXAMPLE 7

The synthesis of [N$^a$MeTyr$^1$, C$^a$Me-D-Tyr$^{10}$, D-Lys$^{21}$, Nle$^{27}$]-hGRF(1-29)-NH$_2$ having the formula: N$^a$MeTyr-Ala-Asp-Ala-Ile-Phe-Thr-Asn-Ser-C$^a$Me-D-Tyr-Arg -Lys-Val-Leu-Gly-Gln-Leu-Ser-Ala-Arg-D-Lys-Leu-Leu-Gln -Asp-Ile-Nle-Ser-Arg-NH2 is conducted in a stepwise manner using a Beckman 990 Peptide Synthesizer on an MBHA resin as in Example 1. The peptide is judged to be substantially pure using TLC and HPLC.

EXAMPLE 8

The synthesis of [D-NMA$^2$, CML$^5$, D-Lys$^{21}$, Nva$^{27}$]-rGRF(1-29)-NH2 having the formula: H-His-D -NMA-Asp-Ala-CML-Phe-Thr-Asn-Ser-Tyr-Arg-Arg-Ile-Leu-Gly-Gln -Leu-Tyr-Ala-Arg-D-Lys-Leu-Leu-His-Glu-Ile-Nva-Asn-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 9

The synthesis of [D-Phe$^1$, D-NMA$^2$, Glu8, C$^a$Me-Tyr$^{10}$, Ile$^{13}$, CML$^{22}$]-hGRF(1-32)-NH$_2$ having the formula:

H-D-Phe-D-NMA-Asp-Ala-Ile-Phe-Thr-Glu-Ser-C$^a$MeTyr-Arg-Lys -Ile-Leu-Gly-Gln-Leu-Ser-Ala-Arg-Lys-CML-Leu-Gln-Asp-Ile -Met-Ser-Arg-Gln-Gln-Gly-NH2 is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 10

The synthesis of [pCl-Phe$^1$, D-NMA$^2$, CMA19, VAl$^{22}$, Asp$^{25}$, Ile$^{27}$]-rGRF(1-29)-NH$_2$ having the formula: H-pCl-Phe-D-NMA-Asp-Ala-Ile-Phe-Thr -Ser-Ser-Tyr-Arg-Arg-Ile-Leu-Gly-Gln-Leu-Tyr-CMA-Arg-Lys -Val-Leu-His-Asp-Ile-Ile-Asn-Arg-NH$_2$ is conducted in a stepwise manner using a Beckman 990 Peptide Synthesizer on an MBHA resin, in the manner generally described in Example 1. The peptide is judged to be substantially pure using TLC and HPLC.

EXAMPLE 11

The synthesis of [CML$^1$, D-NMA$^2$, D-Asp$^3$, CMA$^{22}$]-hGRF(1-32)-NH$_2$ having the formula: H-CML-D -NMA-D-Asp-Ala-Ile-Phe-Thr-Lys-Ser-Tyr-Arg-Lys-Val-Leu-Gly -Gln-Leu-Ser-Ala-Arg-Lys-CMA-Leu-Gln-Asp-Ile-Met-Ser-Arg -Gln-Gln-Gly-NH2 is conducted in a stepwise manner using a Beckman 990 Peptide Synthesizer on an MBHA resin as in Example 1. This analog is judged to be substantially pure using TLC and HPLC.

EXAMPLE 12

The synthesis of [D-Tyr$^1$, D-NMA$^2$, D-Asp$^3$, C$^a$Me-D-Tyr$^{10}$, Ala$^{15}$, CML$^{22}$, D-Met$^{27}$]-hGRF (1-29)-NH$_2$ having the formula: H-D-Tyr-D-NMA-D -Asp-Ala-Ile-Phe-Thr-Asn-Ser-C$^a$Me-D-Tyr-Arg-Lys-Val-Leu -Ala-Gln-Leu-Ser-Ala-Arg-D-Arg-CML-Leu-Gln-Asp-Ile -D-Met-Ser-Arg-NH$_2$ is conducted in a stepwise manner using a Beckman 990 Peptide Synthesizer on an MBHA resin as in Example 1. This analog is judged to be substantially pure using TLC and HPLC.

EXAMPLE 13

The synthesis of [D-His$^1$, D-NMA$^2$, Lys$^8$, CML$^{13}$, Ala$^{27}$]-rGRF(1-29)-NH$_2$ having the formula: H-D-His-D-NMA-Asp-Ala-Ile-Phe-Thr-Lys-Ser-Tyr-Arg -Arg-CML-Leu-Gly-Gln-Leu-Tyr-Ala-Arg-Lys-Leu-Leu-His-Glu -Ile-Ala-Asn-Arg-NH$_2$ is conducted in a step-

EXAMPLE 14

The synthesis of a rGRF analog fragment i.e. [N$^a$MeTyr$^1$, D-NMA$^2$, Glu$^8$, CMA$^{13}$, D-Arg$^{21}$, C$^a$MeIle22]-rGRF (1-29)-NH$_2$ having the formula: N$^a$MeTyr-D-NMA-Asp -Ala-Ile-Phe-Thr-Glu-Ser-Tyr-Arg-Arg-CMA-Leu-Gly-Gln-Leu -Tyr-Ala-Arg-D-Arg-C$^a$MeIle-Leu-His-Glu-Ile-Met-Asn-Arg -NH$_2$ is conducted in a stepwise manner using a Beckman 990 Peptide Synthesizer on an MBHA resin as in Example 1. The peptide is judged to be substantially pure using TLC and HPLC.

EXAMPLE 15

The synthesis of [CML$^1$, D-NMA$^2$, Leu$^{13}$, CMA$^{19,22}$, Ala$^{27}$]-rGRF-(1-29)- NH$_2$ having the formula: H-CML-D-NMA-Asp-Ala-Ile-Phe-Thr-Ser-Ser-Tyr-Arg -Arg-Leu-Leu-Gly-Gln-Leu-Tyr-CMA-Arg-Lys-CMA-Leu-His-Glu -Ile-Ala-Asn-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 16

The synthesis of [C$^a$MePhe$^1$, NMA$^2$, Lys$^8$, Arg$^{12}$, Ile$^{13}$, CMA$^{19}$Ile$^{27}$]-hGRF(1-29)-NH$_2$ having the formula: H-C$^a$MePhel-NMA-Asp-Ala-Ile-Phe-Thr-Lys-Ser -Tyr-Arg-Arg-Ile-Leu-Gly-Gln-Leu-Ser-CMA-Arg-Lys-Leu-Leu -Gln-Asp-Ile-Ile-Ser-Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 17

The synthesis of [desaminoD-Tyr$^1$, D-NMA$^2$, Arg$^8$,-Phe$^{10}$, C$^a$MeVa1$^{13}$, Leu$^{27}$, Asn$^{28}$]-hGRF (1-29)-NH$_2$ having the formula: desNH$_2$ -D-Tyr-D-NMA-Asp -Ala-Ile-Phe-Thr-Arg-Ser-Phe-Arg-Lys-C$^a$MeVal-Leu-Gly -Gln-Leu-Ser-Ala-Arg-Lys-Leu-Leu-Gln-Asp-Ile-Leu-Asn -Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC. cl EXAMPLE 18

The synthesis of [D-NMA$^2$, C$^a$MeTyr$^{10}$, C$^a$MeVal$^{13}$, CML$^{22}$, Nle$^{27}$, Asn$^{28}$]-hGRF(1-29)-NH$_2$ having the formula: H-Tyr-D-NMA-Asp-Ala-Ile-Phe-Thr -Asn-Ser-C$^a$MeTyr-Arg-Lys-C$^a$MeVal-Leu-Gly-Gln-Leu-Ser -Ala-Arg-Lys-CML-Leu-Gln-Asp-Ile-Nle-Asn-Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 19

The synthesis of [C$^a$MePhel, D-NMA$^2$, Ca C$^a$MeIle$^{13}$, Val$^{27}$]-rGRF(1-29)-NH$_2$ having the formula: H-C$^a$MePhe-D-NMA-Asp-Ala-Ile-Phe-Thr -Ser-C$^a$MeTyr-Arg-Arg-C$^a$MeIle-Leu-Gly-Gln-Leu-Tyr -Ala-Arg-Lys-Leu-Leu-His-Glu-Ile-Val-Asn-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 20

The synthesis of [desaminoD-Met$^1$, D-NMA$^2$, C$^a$MeTyr$^{10}$, C$^a$MeVal$^{13}$, CMA$^{19}$, Asn$^{28}$]-hGRF(1-44)-NH$_2$ having the formula: desNH$_2$ -D-Met-D-NMA-Asp-Ala-Ile-Phe -Thr-Asn-Ser-C$^a$MeTyr-Arg-Lys-C$^a$MeVal-Leu-Gly-Gln-Leu -Ser-CMA-Arg-Lys-Leu-Leu-Gln-Asp-Ile-Met-Asn-Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 21

The synthesis of [N$^a$MeHis$^1$, D-NMA$^2$, C$^a$MeVal$^{13}$-Nle$^{27}$]-hGRF(1-29)-NH$_2$ having the formula: N$^a$MeHis-D -NMA-Asp-Ala-Ile-Phe-Thr-Asn-Ser-Tyr-Arg-Lys-C$^a$MeVal-Leu -Gly-Gln-Leu-Ser-Ala-Arg-Lys-Leu-Leu-Gln-Asp-Ile-Nle-Ser -Arg-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 22

The synthesis of the hGRF analog fragment, [For-Tyr$^1$, D-NMA$^2$, C$^a$MeTyr$^{10}$, CMA$^{19}$, Leu$^{27}$, Asn$^{28}$]-hGRF(1-32)-NH$_2$ having the formula: For-Tyr-D-NMA-Asp-Ala-Ile-Phe-Thr-Asn-Ser-C$^a$MeTyr-Arg-Lys -Val-Leu-Gly-Gln-Leu-Ser-CMA-Arg-Lys-Leu-Leu-Gln-Asp-Il e-Leu-Asn-Arg-Gln-Gln-Gly-NH$_2$ is conducted in a stepwise manner using a Beckman 990 Peptide Synthesizer on an MBHA resin as in Example 1. This analog is judged to be substantially pure using TLC and HPLC.

EXAMPLE 23

The synthesis of [D-NMA$^2$, Lys$^{12}$, C$^a$MeIle$^{13}$, CMA$^{19}$, Nle$^{27}$]-rGRF(1-29)-NH$_2$, having the formula: H-His-D-NMA-Asp-Ala-Ile-Phe-Thr-Ser-Ser-Tyr-Arg -Lys-C$^a$MeIle-Leu-Gly-Gln-Leu-Tyr-CMA-Arg-Lys-Leu -Leu-His-Glu-Ile-Nle-Asn-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 24

The synthesis of the hGRF analog fragment [D-NMA$^2$, Arg$^{12}$, CML$^{22}$, Ile$^{27}$]-hGRF(1-29)-NH$_2$ having the formula: H-Tyr-D-NMA-Asp-Ala-Ile-Phe-Thr-Asn -Ser-Tyr-Arg-Arg-Val-Leu-Gly-Gln-Leu-Ser-Ala-Arg-Lys -CML-Leu-Gln-Asp-Ile-Ile-Ser-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 25

The synthesis of [D-Phe$^1$, D-NMA$^2$, C$^a$MeVal$^{13}$, Ala$^{15}$, CML$^{22}$, D-Met$^{27}$]-hGRF(1-29)-NH$_2$ having the formula: H-D-Phe-D-NMA-Asp-Ala-Ile-Phe-Thr-Asn -Ser-Tyr-Arg-Lys-C$^a$MeVal-Leu-Ala-Gln-Leu-Ser-Ala-Arg -Lys-CML-Leu-Gln-Asp-Ile-D-Met-Ser-Arg-NH$_2$ is conducted in a stepwise manner using a Beckman 990 Peptide Synthesizer on an MBHA resin as in Example 1. This analog is judged to be substantially pure using TLC and HPLC.

EXAMPLE 26

The synthesis of [D-NMA², D-Arg²¹, CML22]-hGRF(1-32)-NH₂ having the formula: H-Tyr-D-NMA-Asp -Ala-Ile-Phe-Thr-Asn-Ser-Tyr-Arg-Lys-Val-Leu-Gly-Gln-Leu-Ser -Ala-Arg-D-Arg-CML-Leu-Gln-Asp-Ile-Met-Ser-Arg-Gln -Gln-Gly-NH₂ is conducted in a stepwise manner using a Beckman 990 Peptide Synthesizer on an MBHA resin as in Example 1. This analog is judged to be substantially pure using TLC and HPLC.

EXAMPLE 27

The synthesis of [desaminoHis¹, D-NMA², Lys⁸, Asp²⁵, CML²⁶]-rGRF(1-29)-NH₂ having the formula: desNH₂ His-D-NMA-Asp-Ala-Ile-Phe-Thr-Lys-Ser-Tyr-Arg-Arg-Ile -Leu-Gly-Gln-Leu-Tyr-Ala-Arg-Lys-Leu-Leu-His-Asp-CML-Met -Asn-Arg-Nh₂ is conducted in a stepwise manner using a Beckman 990 Peptide Synthesizer on an MBHA resin as in Example 1. The peptide is judged to be substantially pure using TLC and HPLC.

EXAMPLE 28

The synthesis of [Ac-D-His¹, D-NMA²,Arg⁸, CᵅMe-Tyr¹⁰, CMA¹³, Nle²⁷]-rGRF(1-29)-NH₂ having the formula: Ac-D-His-D-NMA-Asp-Ala-Ile-Phe-Thr-Arg-Ser-CᵅMetyr-Arg-Arg-CMA-Leu-Gly-Gln-Leu-Tyr-Ala-Arg-Lys-Leu-Leu His-Glu-Ile-Nle-Asn-Arg-NH₂ is conducted in a stepwise manner using a Beckman 990 Peptide Synthesizer on an MBHA resin, in the manner generally described in Example 1. The peptide is judged to be substantially pure using TLC and HPLC.

EXAMPLE 29

The synthesis of [D-Ala², D-Asp³, CᵅMeTyr¹⁰, CMA¹⁹, CML²², Leu²⁷]-hGRF(1-32)-NH₂ having the formula: H-Tyr-D-Ala-D-Asp-Ala-Ile-Phe-Thr-Asn-Ser-CᵅMeTyr-Arg-Lys -Val-Leu-Gly-Gln-Leu-Ser-CMA-Arg-Lys-CML-Leu-Gln-Asp-Ile -Leu-Ser-Arg-Gln-Gln-Gly-NH₂ is conducted in a stepwise manner using a Beckman 990 Peptide Synthesizer on an MBHA resin as in Example 1. This analog is judged to be substantially pure using TLC and HPLC.

EXAMPLE 30

The synthesis of [D-Tyr¹, D-NMA², CML⁵, Lys⁸, CᵅMe-D-Tyr¹⁰, Ala¹⁵, D-Met²⁷]-hGRF(1-29)-NH₂ having the formula: H-D-Tyr-D-NMA-Asp-Ala-CML-Phe-Thr-Lys -Ser-CᵅMe-D-Tyr-Arg-Lys-Val-Leu-Ala-Gln-Leu-Ser-Ala-Arg -Lys-Leu-Leu-Gln-Asp-Ile-D-Met-Ser-Arg-NH₂ is conducted in a stepwise manner using a Beckman 990 Peptide Synthesizer on an MBHA resin as in Example 1. This analog is judged to be substantially pure using TLC and HPLC.

EXAMPLE 31

The synthesis of [D-His¹, D-NMA², Arg⁸,1 Leu¹³, CMA¹⁹, Nle²⁷]-rGRF(1-32)-NH₂ having the formula: H-D-His-D-NMA-Asp-Ala-Ile-Phe-Thr-Arg-Ser -Tyr-Arg-Arg-Leu-Leu-Gly-Gln-Leu-Tyr-CMA-Arg-Lys -Leu-Leu-His-Glu-Ile-Nle-Asn-Arg-Gln-Gln-Gly-NH₂ is conducted in a stepwise manner using a Beckman 990 Peptide Synthesizer on an MBHA resin, in the manner generally described in Example 1. The peptide is judged to be substantially pure using TLC and HPLC.

EXAMPLE 32

The synthesis of a rGRF analog fragment i.e. [desaminoTyr¹, CML22]-rGRF(1-29)-NH₂ having the formula: desNH₂ Tyr-Ala-Asp-Ala-Ile-Phe-Thr-Ser -Ser-Tyr-Arg-Arg-Ile-Leu-Gly-Gln-Leu-Tyr-Ala-Arg-Lys-CML Leu-His-Glu-Ile-Met-Asn-Arg-NH₂ is conducted in a stepwise manner using a Beckman 990 Peptide Synthesizer on an MBHA resin as in Example 1. The peptide is judged to be substantially pure using TLC and HPLC.

EXAMPLE 33

The synthesis of [Ac-D-Tyr¹, D-NMA², CᵅMe-TyR¹⁰, CᵅMeVal¹³, CMA¹⁹, CML²², Nle²⁷]-hGRF(1-29)-NH₂ having the formula: Ac-D-Tyr-D-NMA-Asp-Ala-Ile-Phe-Thr-Asn -Ser-CᵅMeTyr-Arg-Lys-CᵅMe-Val-Leu-Gly-Gln-Leu-Ser-CMA -Arg-Lys-CML-Leu-Gln-Asp-Ile-Nle-Ser-Arg-NH₂ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 34

The synthesis of [CML¹, D-NMA², Glu⁸, CMA¹⁹, Glu²⁵, Ile²⁷]-rGRF(1-29)-NH₂ having the formula: H-CML-D-NMA-Asp-Ala-Ile-Phe-Thr-Glu-Ser-Tyr-Arg-Arg-Ile-Leu -Gly-Gln-Leu-Tyr-CMA-Arg-Lys-Leu-Leu-His-Glu-Ile-Ile-Asn -Arg-NH₂ is conducted in a stepwise manner using a Beckman 990 Peptide Synthesizer on an MBHA resin as in Example 1. The peptide is judged to be substantially pure using TLC and HPLC.

EXAMPLE 35

The synthesis of [For-D-Tyr¹, D-NMA², CᵅMeVal¹³, CMA¹⁹, CML²², Asn²⁸]-hGRF(1-29)-NH₂ having the formula: For-D-Tyr-D-NMA-Asp-Ala-Ile-Phe-Thr-Asn-Ser -Tyr-Arg-Lys-CᵅMeVal-Leu-Gly-Gln-Leu-Ser-CMA-Arg-Arg -CML-Leu-Gln-Asp-Ile-Met-Asn-Arg-NH₂ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE 36

The synthesis of [NMA², CᵅMeVal¹³, Nle²⁷]-hGRF(1-29)-NH₂ having the formula: H-Tyr-NMA-Asp-Ala -Ile-Phe-Thr-Asn-Ser-Tyr-Arg-Lys-CᵅMe-Val-Leu-Gly-Gln-Leu Ser-Ala-Arg-Lys-Leu-Leu-Gln-Asp-Ile-Nle-Ser-Arg-NH₂ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC. The acetate salt is then prepared by dissolving the peptide in water and adding lN acetic acid. The resulting solution is lyophilized to yield the acetate salt.

EXAMPLE 37

The synthesis of the hGRF analog [D-NMA², Arg⁸, CMA¹⁹, CML²², Nle²⁷]-hGRF(1-32)-NH₂ having the formula: H-Tyr-D-NMA-Asp-Ala-Ile-Phe-Thr-Arg-Ser-Tyr -Arg-Lys-Val-Leu-Gly-Gln-Leu-Ser-CMA- Arg-Lys-CML-Leu-Gln -Asp-Ile-Nle-Ser-Arg-Gln-Gln-Gly-NH$_2$ is conducted in a stepwise manner using a Beckman 990 Peptide Synthesizer on an MBHA resin as in Example 1. This analog is judged to be substantially pure using TLC and HPLC.

EXAMPLE 38

The synthesis of [CML$^{17}$Nle$^{27}$]-rGRF(1-29)-NH$_2$, having the formula: H-His-Ala-Asp-Ala -Ile-Phe-Thr-Ser-Ser-Tyr-Arg-Arg-Ile-Leu-Gly-Gln-CML-Tyr -Ala-Arg-Arg-Leu-Leu-His-Glu-Ile-Nle-Asn-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 39

The synthesis of the hGRF analog [D-NMA$^2$, C$^a$Me-Val$^{13}$, CMA$^{19}$, CML$^{22}$, Nle27, Asn28]-hGRF(1-29)-NH$_2$ having the formula: H-Tyr-D-NMA-Asp-Ala-Ile-Phe-Thr-Asn-Ser -Tyr-Arg-Lys-C$^a$MeVal-Leu-Gly-Gln-Leu-Ser-CMA-Arg-Lys-CML -Leu-Gln-Asp-Ile-Nle-Asn-Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 40

The synthesis of [N$^a$MeTyr$^1$, Ala$^{15}$, CML$^{26}$, Nle$^{27}$, Asn$^{28}$]-hGRF(1-29)-NH$_2$ having the formula: N$^a$Me-Tyr-Ala-Asp-Ala-Ile-Phe-Thr-Asn-Ser-Tyr-Arg-Lys-Val-Leu -Ala-Gln-Leu-Ser-Ala-Arg-Lys-Leu-Leu-Gln-Glu-CML-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = -43.5 \pm 1$ (c=1, 1% acetic acid).

EXAMPLE 41

The synthesis of [Met$^1$, CMA19, Arg$^{21}$, Nle$^{27}$]-rGRF(1-29)-NH$_2$ having the formula: H-Met-Ala-Asp-Ala-Ile-Phe-Thr-Ser-Ser-Tyr-Arg-Arg-Ile-Leu-Gly -Gln-Leu-Tyr-CMA-Arg-Arg-Leu-Leu-His-Glu-Ile-Nle-Asn-Ar g-NH$_2$ is conducted in a stepwise manner using a Beckman 990 Peptide Synthesizer on an MBHA resin as in Example 1. The peptide is judged to be substantially pure using TLC and HPLC.

EXAMPLE 42

The synthesis of [pCl-Phe$^1$, D-NMA$^2$, C$^a$MeTyr$^{10}$, CMA$^{19}$, Arg$^{21}$, Nle$^{27}$]-rGRF(1-43)-OH having the formula: H-pCl-Phe-D-NMA-Asp-Ala-Ile-Phe-Thr-Ser -Ser-C$^a$MeTyr-Arg-Arg-Ile-Leu-Gly-Gln-Leu-Tyr-CMA -Arg-Arg-Leu-Leu-His-Asp-Ile-Nle-Asn-Arg-Gln-Gln -Gly-Glu-Arg-Asn-Gln-Glu-Gln-Arg-Ser-Arg-Phe-Asn-OH is conducted in a stepwise manner using a Beckman 990 Peptide Synthesizer on a chloromethylated resin as in Example 3. The peptide is judged to be substantially pure using TLC and HPLC.

EXAMPLE 43

The synthesis of [N$^a$MeTyr$^1$, Ala$^{15}$, CML$^{23}$, Nle$^{27}$, Asn$^{28}$]-hGRF(1-29)-NH$_2$ having the formula: N$^a$Me-Tyr-Ala-Asp-Ala-Ile-Phe-Thr-Asn-Ser-Tyr-Arg-Lys-Val-Leu -Ala-Gln-Leu-Ser-Ala-Arg-Lys-Leu-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = -44.0 \pm 1$ (c=1, 1% acetic acid).

EXAMPLE 44

The synthesis of [N$^a$MeTyr$^1$, CML$^{13}$, Ala$^{15}$, Nle$^{27}$, Asn$^{28}$]-hGRF(1-29)-NH$_2$ having the formula: N$^a$Me-Tyr-Ala-Asp-Ala-Ile-Phe-Thr-Asn-Ser-Tyr-Arg-Lys-CML-Leu -Ala-Gln-Leu-Ser-Ala-Arg-Lys-Leu-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 45

The synthesis of [N$^a$MeTyr$^1$, Ala$^{15}$, CMA$^{19}$, Nle$^{27}$, Asn$^{28}$]-hGRF(1-29)-NH$_2$ having the formula: N$^a$Me-Tyr-Ala-Asp-Ala-Ile-Phe-Thr-Asn-Ser-Tyr-Arg-Lys-Val-Leu -Ala-Gln-Leu-Ser-CMA-Arg-Lys-Leu-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = -45.5 \pm 1$ (c=1, 1% acetic acid).

EXAMPLE 46

The synthesis of [N$^a$MeTyr$^1$, Ala$^{15}$, CML$^{17}$, Nle$^{27}$, Asn$^{28}$]-hGRF(1-29)-NH$_2$ having the formula: N$^a$Me-Tyr-Ala-Asp-Ala-Ile-Phe-Thr-Asn-Ser-Tyr-Arg-Lys-Val-Leu -Ala-Gln-CML-Ser-Ala-Arg-Lys-Leu-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = 49.0° \pm 1$ (c=1, 1% acetic acid).

EXAMPLE 47

The synthesis of [N$^a$MeTyr$^1$, Ala$^{15}$, CML$^{22}$, Nle$^{27}$, Asn$^{28}$]-hGRF(1-29)-NH$_2$ having the formula: N$^a$Me-Tyr-Ala-Asp-Ala-Ile-Phe-Thr-Asn-Ser-Tyr-Arg-Lys-Val-Leu -Ala-Gln-Leu-Ser-Ala-Arg-Lys-CML-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = -44.0 \pm 1$ (c=1, 1)% acetic acid).

EXAMPLE 48

The synthesis of [N$^a$MeTyr$^1$, CMA$^{13}$, Ala$^{15}$, Nle$^{27}$, Asn$^{28}$]-hGRF(I-29)-NH$_2$ having the formula: N$^a$Me-Tyr-Ala-Asp-Ala-Ile-Phe-Thr-Asn-Ser-Tyr-Arg-Lys-CMA-Leu -Ala-Gln-Leu-Ser-Ala-Arg-Lys-Leu-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = -47.0 \pm 1$ (c=1, 1% acetic acid).

EXAMPLE 49

The synthesis of [N$^\alpha$MeTyr$^1$, CML$^5$, Ala$^{15}$, Nle$^{27}$, Asn$^{28}$ ]-hGRF(1-29)-NH$_2$ having the formula: N$^\alpha$Me-Tyr-Ala-Asp-Ala-CML-Phe-Thr-Asn-Ser-Tyr-Arg-Lys-Val-Leu -Ala-Gln-Leu-Ser-Ala-Arg-Lys-Leu-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC. The optical rotation of the purified peptide is measured using a photoelectric polorimeter and found to be $[\alpha]_D = -45.0 \pm 1$ (c=1, 1% acetic acid).

EXAMPLE 50

The synthesis of [N$^\alpha$MeTyr$^1$, CML$^{5,13,17,22,27}$, Ala$^{15}$, CMA$^{19}$, Asn$^{28}$ ]-hGRF(1-29)-NH$_2$ having the formula: N$^\alpha$MeTyr-Ala-Asp-Ala-CML-Phe-Thr-Asn-Ser-Tyr-Arg-Lys-CML-Leu -Ala-Gln-CML-Ser-CMA-Arg-Lys-CML-Leu-Gln-Glu-Ile-CML-Asn -Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 51

The synthesis of [N$^\alpha$MeTyr$^1$, Ala$^{15}$, CML$^{22,27}$, Asn$^{28}$ ]-hGRF(1-29)-NH$_2$ having the formula: N$^\alpha$MeTyr-Ala-Asp-Ala-Ile-Phe-Thr-Asn-Ser-Tyr-Arg-Lys-Val-Leu -Ala-Gln-Leu-Ser-Ala-Arg-Lys-CML-Leu-Gln-Glu-Ile-CML-Asn -Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 52

The synthesis of [N$^\alpha$MeTyr$^1$, Ala$^{15}$, CMA$^{19}$, CMA$^{22}$, Nle$^{27}$, Asn$^{28}$ ]-hGRF(1-29)-NH$_2$ having the formula: N$^\alpha$MeTyr-Ala-Asp-Ala-Ile-Phe-Thr-Asn-Ser-Tyr-Arg-Lys-Val-Leu -Ala-Gln-Leu-Ser-CMA-Arg-Lys-CML-Leu-Gln-Glu-Ile-Nle-Asn -Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 53

The synthesis of [N$^\alpha$MeTyr$^1$, Ala$^{15}$, CML$^{17,22,27}$, CMA$^{19}$, Asn$^{28}$ ]-hGRF(1-29)-NH$_2$ having the formula: N$^\alpha$MeTyr-Ala-Asp-Ala-Ile-Phe-Thr-Asn-Ser-Tyr-Arg-Lys-Val-Leu -Ala-Gln-CML-Ser-CMA-Arg-Lys-CML-Leu-Gln-Glu-Ile-CML-Asn -Arg-NH$_2$ is conducted in a stepwise manner using a Beckman 990 Peptide Synthesizer on an MBHA resin as in Example 1. The peptide is judged to be substantially pure using TLC and HPLC.

EXAMPLE 54

The synthesis of a 40-residue amidated peptide [C$^\alpha$MeHis$^1$, D-NMA$^2$, CML27]-hGRF(1-44)-NH$_2$ having the formula: H-C$^\alpha$MeHis-D-NMA-Asp-Ala-Ile-Phe-Thr-Asn-Ser -Tyr-Arg-Lys-Val-Leu-Gly-Gln-Leu-Ser-Ala-Arg-Lys-Leu-Leu -Gln-Asp-Ile-CML-Ser-Arg-Gln-Gln-Gly-Glu-Ser-Asn-Gln-Glu -Arg-Gly-Ala-Arg-Ala-Arg-Leu-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

The synthetic peptides prepared in the Examples are compared with synthetic hpGRF(1-40)-OH in in vitro assays and are found to exhibit generally greater potencies for the secretion of GH and similar intrinsic activities. All of these synthetic peptides are considered to be biologically active and potentially useful for stimulating the release of GH by the pituitary.

To determine the relative effectiveness of certain representative synthetic peptides to promote the release of growth hormone, in vitro assays are carried out using synthetic hpGRF(1-40)-OH as a standard in side-by-side comparison with equimolar concentrations of the representative analogs which have been synthesized. Cultures are used which include cells of rat pituitary glands removed some three to five days previously. Such cultures are considered optimal for the secretion of growth hormone and are used for the comparative testing, in the general manner described in Vale et al. *Endocrinology*, 91, 562–572 (1972) and as more particularly described in Vale et al. *Endocrinology*, 112, 1553–1555 (1983). Incubation with the substance to be tested is carried out for 3 to 4 hours, and aliquots of the culture medium are removed and processed to measure their contents in immunoreactive GH(ir GH) by a well-characterized radioimmunoassay.

The results of this comparative testing for equimolar concentrations are shown in Table I.

TABLE I

| Peptide | In Vitro Potencies |
|---|---|
| hGRF(1–40)—OH (standard for this test) | 1.0 |
| [N$^\alpha$MeTyr$^1$, Ala$^{15}$, CML$^{27}$, Asn$^{28}$]—hGRF(1-29)—NH$_2$. | 10.00 (5.2–20.1) |
| [N$^\alpha$MeTyr$^1$, Ala$^{15}$, CML$^{26}$, Nle$^{27}$, Asn$^{28}$]—hGRF(1-29)—NH$_2$. | 6.44 (4.0–10.3) |
| [N$^\alpha$MeTyr$^1$, Ala$^{15}$, CML$^{23}$, Nle$^{27}$, Asn$^{28}$]—hGRF(1-29)—NH$_2$. | 1.96 (1.1–3.3) |
| [N$^\alpha$MeTyr$^1$, Ala$^{15}$, CML$^{22}$, Nle$^{27}$, Asn$^{28}$]—hGRF(1-29)—NH$_2$. | 7.18 (4.1–12.7) |
| [N$^\alpha$MeTyr$^1$, Ala$^{15}$, CMA$^{19}$, Nle$^{27}$, Asn$^{28}$]—hGRF(1-29)—NH$_2$. | 7.07 (3.8–13.6) |
| [N$^\alpha$MeTyr$^1$, Ala$^{15}$, CML$^{17}$, Nle$^{27}$, Asn$^{28}$]—hGRF(1-29)—NH$_2$. | 5.41 (3.5–8.3) |
| [N$^\alpha$MeTyr$^1$, CMA$^{13}$, Ala$^{15}$, Nle$^{27}$, Asn$^{28}$]—hGRF(1-29)—NH$_2$. | 2.24 (1.4–3.4) |
| [N$^\alpha$MeTyr$^1$, CML$^5$, Ala$^{15}$, Nle$^{27}$, Asn$^{28}$]—hGRF(1-29)—NH$_2$. | 3.59 (2.3–5.5) |

In addition to the in vitro tests for secretion of growth hormone, in vivo experiments inject the synthetic peptides intravenously into urethane-anesthetized male rats and determine that they suppress spontaneous GH secretion without abolishing the response to exogenous GRF. Blood samples are taken immediately prior to, and 10, 30 and 60 minutes after injections, and GH levels in blood are measured by radioimmunoassay. This in vivo testing of these synthetic peptides shows that each has greater biological potency than that exhibited by hpGRF(1-40)-OH and has substantially longer duration of effectiveness, which is shown in blood levels of pituitary GH when measured at both 30 and 60 min. after IV injection. Other known GRF in vivo tests that are known to be effective to detect secretion of GH are used to confirm these results. Dosages between about 500 nanograms and about 50 micrograms of these peptides per Kg. of body weight are considered to be effective in causing GH secretion.

Such synthetic hGRF analogs and possibly rGRF analogs should be useful for human applications in which a physician wishes to elevate GH production.

Stimulation of GH secretion by such analogs is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals, such as chickens, turkeys, pigs, goats, cattle and sheep, and may be used in aquiculture for raising fish and other cold-blooded marine animals, e.g. sea turtles and eels, and amphibians, to accelerate growth and increase the ratio of protein to fat gained by feeding effective amounts of the peptides.

For administration to humans, these synthetic peptides should have a purity of at least about 93% and preferably at least 98%. Purity, for purposes of this application, refers to the intended peptide constituting the stated weight % of all peptides and peptide fragments present. For the administration of such synthetic peptides to commercial and other animals in order to promote growth and reduce fat content, lower purities may be acceptable.

These synthetic peptides or the nontoxic salts thereof, combined with a pharmaceutically or veterinarily acceptable carrier to form a pharmaceutical composition, may be administered to animals, including humans, either intravenously, subcutaneously, intramuscularly, percutaneously, e.g. intranasally or even orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parenteral dosage will be from about 0.01 to about 1 microgram of the peptide per kilogram of the body weight of the host.

It may also be desirable to deliver such a peptide over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts. A relatively insoluble salt may also be formulated in a gel, for example, an aluminum stearate gel. A suitable slow release depot formulation for injection may also contain the peptide or a salt thereof dispersed or encapsulated in a slow degrading, non-toxic or non-antigenic polymer, such as a polylactic acid/polyglycolic acid polymer, for example, as described in U.S. Pat. No. 3,773,919. These compounds may also be formulated into silastic implants.

It is also possible to administer the peptides transdermally to humans over an extended period of time using electrical current, as reported in Meyer, B.R. et al., Clin. Pharm. & Therapeutics, 44, 6, 607–612 (1988). For example, transdermal patches can be used which utilize a 9-volt battery to continuously apply about 0.2 milliamp current to human skin and which hereby effectively deliver the peptides through the epidermis into the bloodstream.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminus of the peptide and extending to about position-29, can be made in accordance with the known experimental practises to date to create peptides or peptide fragments that retain all or very substantial portions of the biological potency of the peptide, and such peptides are considered as being within the scope of the invention. Moreover, additions may be made to either terminus, or to both terminals, and/or generally equivalent residues can be substituted for naturally occurring residues, as is well-known in the overall art of peptide chemistry, to produce other analogs having at least a substantial portion of the potency of the claimed polypeptide without deviating from the scope of the invention. Moreover, modifications may be made to the preferred —$NH_2$ group at the C-terminus in accordance with the state of this art today; for example, the carboxyl moiety of the amino acid residue at the C-terminus can be the radical —COOR,—CRO,—CONHNHR,—CON(R)(R') or -$CH_2$OR, with R and R' being lower alkyl, fluoro lower alkyl or hydrogen, without deviating from the invention for such modifications result in equivalent synthetic peptides.

Various features of the invention are emphasized in the claims which follow.

What is claimed is:

1. A peptide having the formula:
   [$N^\alpha MeTyr^1$, $Ala^{15-7}$, $CML^{26}$, $Nle^{27}$, $Asn^{28}$]-hGRF(1-290-$NH_2$;
   [$N^\alpha MeTyr^1$, $Ala^{15}$, $CML^{22}$, $Nle^{27}$, $Asn^{28}$]-hGRF(1-29)-$NH_2$;
   [$N^\alpha MeTyr^1$, $CML^{5,13,17,22,27}$, $Ala^{15}$, $CMA^{19}$, $Asn^{28}$]-hGRF(1-29)-$NH_2$; or
   [D-$Ala^2$, $CML^{5,13,17,22,27}$, $Ala^{15}$, $CMA^{19}$, $Asn^{28}$]-hGRF(1-29)-$NH_2$.

2. A synthetic peptide having the formula:
   [$N^\alpha MeTyr^1$, $CML^{5,13,17,22,27}$, $Ala^{15}$, $CMA^{19}$, $Asn^{28}$]-hGRF(1-29-1)-$NH_2$, or a non-toxic salt thereof.

* * * * *

UNITED STATES PATENT AND TRADEMARK OFFICE
CERTIFICATE OF CORRECTION

PATENT NO. : 5,098,995
DATED : March 24, 1992
INVENTOR(S) : Rivier, et al

Page 1 of 2

It is certified that error appears in the above-indentified patent and that said Letters Patent is hereby corrected as shown below:

Column 1, line 55, change "$N^{\alpha}CH3$" to --$N^{\alpha}CH_3$--; Column 4, line 14, change "$(Q_6)R^{22}$" to --$(Q_6)R_{22}$--; Column 5, line 19, change "$CH2$" to --$CH_2$--; Column 6, line 16, change "doerth" to --forth--; Column 6, line 39, change "uitable" to --suitable--; Column 6, line 53, change "$CH_2C_{12}$" to --$CH_2Cl_2$--; Column 7, line 3, change "$X_2, X_3, X4$" to --$X^2, X^3, X^4$--; Column 8, line 14, change "roup" to --group--; Column 8, line 58, correct the spelling of "Chromatography"; Column 8, line 68, change "-52.0" to -- -52.0°--; Column 9, lines 7-8, after "Arg" (second occurrence), insert -- -Gln-Gln-Gly-Glu-Ser-Asn-Gln-Glu-Arg --; Column 9, line 54, change "$N^{\alpha}MeHis1$" to --$N^{\alpha}MeHis^1$--; Column 9, lines 58 and 68, change "NH2" to --$NH_2$--; Column 10, lines 8 and 23, change "NH2" to --$NH_2$--; Column 10, line 17, change "Glu8" to --$Glu^8$--; Column 10, lines 30 and 31, change "CMA19, VAl$^{22}$" to --$CMA^{19}$, $Val^{22}$,--; Column 10, lines 41 and 42, after "$D-Asp^3$," insert --$Lys^8$,--; Column 10, line 47, change "NH2" to --$NH_2$--; Column 10, line 54, after "$Ala^{15}$," insert --$D-Arg^{21}$,--; Column 11, line 8, change "$C^{\alpha}MeIle22$" to --$C^{\alpha}MeIle^{22}$--; Column 11, line 31, change "$C^{\alpha}MePhe1$" to --$C^{\alpha}MePhe^1$--; Column 11, line 41, change "$C^{\alpha}MeVal13$" to --$C^{\alpha}MeVal^{13}$--; Column 11, line 62, change "$C^{\alpha}MePhe1$" to --$C^{\alpha}MePhe^1$--; Column 11, line 62, change "Ca" to --$C^{\alpha}MeTyr^{10}$--; Column 13, line 20, change "$Nh_2$" to --$NH_2$--; Column 13, line 30, change "$C^{\alpha}Metyr$" to --$C^{\alpha}MeTyr$--; Column 13, line 62, change "$Arg^{8,1}$" to --$Arg^8$,--; Column 14, line 6, change "CML22" to --$CML^{22}$--; Column 14, line 61, change "IN" to --1N--; Column 15, line 8, change "$CML^{17}Nle^{27}$" to --$CML^{17}$, $Arg^{21}$, $Nle^{27}$--;

UNITED STATES PATENT AND TRADEMARK OFFICE
CERTIFICATE OF CORRECTION

PATENT NO. : 5,098,995
DATED : March 24, 1992
INVENTOR(S) : Rivier, et al

It is certified that error appears in the above-indentified patent and that said Letters Patent is hereby corrected as shown below:

Column 15, line 19, change Nle27, Asn28" to --$Nle^{27}$, $Asn^{28}$--;
Column 15, line 39, change "-43.5" to -- -43.5˚ --;
Column 16, line 5, change "-44.0" to -- -44.0˚ --; Column 16, line 29, change "-45.5" to -- -45.5˚ --; Column 16, line 55, change "-44.0" to -- -44.0˚ --; Column 16, line 68, change "-47.0" to -- -47.0˚ --; Column 17, line 13, change "-45.0" to -- -45.0˚ --; Column 17, line 59, change "CML27" to --$CML^{27}$--;

Column 20, line 58, change "290" to --29)--;
Column 20, line 67, change "(1-29-1)" to --(1-29)--.

Signed and Sealed this

Twenty-first Day of June, 1994

*Attest:*

BRUCE LEHMAN

*Attesting Officer*     Commissioner of Patents and Trademarks